(12) United States Patent
Dwyer et al.

(10) Patent No.: US 7,780,714 B2
(45) Date of Patent: Aug. 24, 2010

(54) IMPLANT DELIVERY APPARATUS

(75) Inventors: Clifford Dwyer, Weston, FL (US); Michael V. Williamson, Jr., Clayton, CA (US); Craig Bonsignore, Pleasanton, CA (US)

(73) Assignee: Cordis Corporation, Miami Lakes, FL (US)

( * ) Notice: Subject to any disclaimer, the term of this patent is extended or adjusted under 35 U.S.C. 154(b) by 521 days.

(21) Appl. No.: 11/264,586

(22) Filed: Nov. 1, 2005

(65) Prior Publication Data
US 2007/0100413 A1 May 3, 2007

(51) Int. Cl.
*A61F 2/06* (2006.01)
(52) U.S. Cl. .................................. 623/1.11
(58) Field of Classification Search ............. 606/108, 606/198; 623/1.11, 1.12; 604/30, 33, 34, 604/236–238, 247, 256; 137/522; 251/294
See application file for complete search history.

(56) References Cited

U.S. PATENT DOCUMENTS

| | | | | |
|---|---|---|---|---|
| 3,699,961 | A * | 10/1972 | Szpur | 604/89 |
| 4,307,731 | A * | 12/1981 | Kaufman | 600/579 |
| 5,489,274 | A * | 2/1996 | Chu et al. | 604/167.05 |
| 5,626,603 | A * | 5/1997 | Venturelli et al. | 623/1.11 |
| 5,667,521 | A * | 9/1997 | Keown | 606/194 |
| 5,676,654 | A | 10/1997 | Ellis | |
| 6,113,608 | A | 9/2000 | Monroe | |
| 6,605,109 | B2 * | 8/2003 | Fiedler | 623/1.12 |
| 2002/0045929 | A1 * | 4/2002 | Diaz | 623/1.11 |
| 2002/0058951 | A1 * | 5/2002 | Fiedler | 606/108 |
| 2003/0004535 | A1 * | 1/2003 | Musbach et al. | 606/194 |
| 2004/0249342 | A1 | 12/2004 | Khosravi | |
| 2006/0030923 | A1 * | 2/2006 | Gunderson | 623/1.11 |
| 2006/0200221 | A1 | 9/2006 | Malewicz | |
| 2006/0271064 | A1 * | 11/2006 | Agnew | 606/108 |
| 2008/0208310 | A1 * | 8/2008 | McDermott et al. | 623/1.11 |

FOREIGN PATENT DOCUMENTS

| | | |
|---|---|---|
| WO | WO 98/57692 A | 12/1998 |
| WO | WO 2006/089517 A | 8/2006 |
| WO | WO 2007/008829 A | 1/2007 |

OTHER PUBLICATIONS

International European Search Report EP 06 25 5624 Date of Completion Aug. 3, 2007.

* cited by examiner

*Primary Examiner*—Anhtuan T Nguyen
*Assistant Examiner*—Jennifer L Hornberger

(57) ABSTRACT

An apparatus for delivering an implant within a lumen or passageway is provided. The apparatus comprises a flexible, hollow outer member having an elongated section that is inserted into and navigated through the lumen of passageway. The implant is mounted within the distal end of the elongated section. An elongated fluid chamber is defined within the outer member between two valves or seals. The valves or seals permit fluid flow in a pre-determined direction during loading of fluid into the chamber, but prevent fluid to exit the chamber during deployment of the implant. A shaft is in contact with the proximal end of the fluid column. During deployment, the shaft is held in a fixed position and the outer member actuated in a proximal direction. The implant exerts compressive forces on the outer member as it is actuated proximally. These forces are transmitted to the fluid column which resists buckling.

13 Claims, 6 Drawing Sheets

IMPLANT DELIVERY APPARATUS

FIELD OF THE INVENTION

This invention generally relates to an apparatus that is used to place a medical device in a pre-selected location within a vessel of a human body. In particular, this invention relates to hydraulic delivery devices for deploying a prosthesis within a vessel.

BACKGROUND OF THE INVENTION

A wide variety of implants are placed at predetermined locations in the human body to repair or prevent damage. A stent is an implant that is generally tubular and is delivered to a pre-determined location in the human body where it is expanded radially in, for example, a vessel or lumen to maintain the patency of the vessel. Stents are widely used in body vessels, body canals, ducts or other body lumens. Stents may take the form of helically wound wire, or tube-like structures with numerous patterns defining the walls of the tubule.

Self-expanding stents are generally cut from a solid tube of superelastic material, such as Nitinol (NiTi) allowing the stent to be deformed and constrained in the deformed condition, then return to the natural condition when unconstrained. For example, one design comprises a solid tube of Nitinol cut to form a series of hoops that are joined together by a plurality of bridges. The bridges are shaped to allow for the frame to flex along its longitudinal and radial directions. The hoops comprise multiple struts. Each adjacent strut is connected together by an apex that allows the frame to assume an expanded diameter when unconstrained.

The delivery systems for stents are generally comprised of catheters with the stent constrained within the distal end of the catheter. It is highly desirable to keep the profile of the catheter as small as possible allowing for easy passage of the catheter through a body lumen. Self-expanding stents can be constrained at a reduced diameter for delivery to the deployment site. Once the stent is deployed, the catheter is removed, leaving the stent implanted at the desired location to maintain vessel patency.

A variety of techniques have been developed for holding a self-expanding stent in a reduced diameter delivery configuration while moving the distal end of the catheter to the deployment site. For example, a common self-expanding prosthesis delivery system employs a sheath to constrain the prosthesis or implant at the distal tip of a concentrically mounted shaft, contained within the sheath. The delivery system is advanced through the vascular system of a patient until it reaches a desired location where the shaft is held in place and the sheath is retracted, allowing the stent to expand.

The shaft is typically fabricated from a coiled metallic component designed to transmit compressive loads from the implant, while maintaining flexibility and minimizing bulk. In addition, the shaft is sufficiently rigid to resist buckling or kinking as the sheath and shaft are moved relative to each other producing frictional forces there-between. Similarly, the sheath or outer member is constructed from a flexible material that allows for navigation of the system through the vasculature of the patient. The sheath must also exhibit sufficient rigidity to handle the tensile load resulting from the frictional interactions between the sheath, prosthesis and shaft as the sheath is retracted toward the proximal end of the shaft.

Frictional and compressive forces limit the functionality of the delivery system. The magnitude of these forces increase with the strength and length of the constrained prosthesis and may be further increased by the addition of pharmaceutical, polymeric or other coatings resulting in an increase in the coefficient of friction between the sheath, prosthesis and shaft. For example, as the length of the stent increases, the shaft must bear a greater compressive load. This requires the shaft to either have a larger diameter or be more rigid to support the compressive load exerted by the prosthesis. Increasing the diameter or rigidity of the shaft results in increased frictional interactions between the shaft and the sheath. This will require a larger force to remove the sheath and deploy the prosthesis.

Several systems have been proposed that increase the deploying force in order to overcome the frictional forces between the shaft and sheath. For example, U.S. Pat. No. 6,113,608—Monroe discloses a delivery apparatus that employs a piston-based hydraulically operated retraction mechanism. The system of Monroe mounts a stent on a receiving region of a shaft that is enclosed by the distal end of a sheath. The sheath is coupled to a piston, located proximal to the sheath. An inflation lumen either supplies or withdraws pressurized fluid to the piston chamber. As the piston moves, the sheath retracts allowing the stent to deploy.

The system of Monroe fails to address several shortcomings inherent in a sheath deployment system. The coefficient of friction between the sheath, shaft and prosthesis remains unchanged. Merely increasing the deployment force for pulling back the sheath will not mitigate, and instead, will increase the buckling force exerted on the shaft. As the sheath is withdrawn the shaft may "kink" causing the prosthesis, or the vasculature to be damaged.

One approach to prevent the shaft from kinking is to employ a more rigid material. As the rigidity of the shaft increases, it loses flexibility. This makes it difficult to maneuver the delivery device within the vascular system of the patient. Another approach is to simply increase the diameter of the shaft. This will also make it difficult to navigate through the vasculature of the patient. It is also desirable to keep the profile of the delivery system as small as possible, especially when navigating through small vessels.

Yet another alternative is to vary the construction of the shaft along its length creating rigidity zones. For example sections of the support are constructed from a more rigid material while adjoining sections are constructed from a more flexible material. This approach provides for increased flexibility, however, the more rigid sections of the shaft could prove difficult to navigate through small vasculature. Moreover, constructing the shaft from more than one type of material is expensive. Currently, there is no apparatus, delivery system for the deployment of a prosthesis within the vasculature of a body that is highly flexible, has a low profile and can withstand high frictional and compressive forces encountered during deployment of the prosthesis. The present invention is designed to address these and other needs.

SUMMARY OF THE INVENTION

According to the invention, an apparatus for delivering an implant within a lumen or passageway is provided. The apparatus comprises a flexible, hollow outer member having an elongated region that is sufficiently narrow for insertion into, and navigation through, a lumen. An implant is mounted within the distal end of the elongated region. Also included within the outer member is a chamber that is located between the implant and a proximal region of the outer member. The chamber is filled with a biocompatible liquid to form an elongated liquid column.

The outer member includes an elongated section or region having the implant mounted at its distal end. The elongated section has a cross section that allows for passage through a body lumen. In one embodiment of the invention, the first region comprises a substantially cylindrical sheath constructed from a flexible material that is capable of bending during navigation through the lumen, yet can withstand tensile loads exerted by an implant contained therein, for example, a self expanding stent. The outer member also includes a truncated second section or region, located proximal to the elongated first region. The second section has an expanded cross section and serves as a handle for steering the elongated section through the lumen. In addition, a port is located in the truncated region that is in fluid communication with the inner portion of the outer member.

The implant is mounted within the distal end of the elongated section or region. In one embodiment of the invention, the implant is mounted on a support. If the implant comprises a self-expanding stent, the support member carries the compressive load of the stent when it is contracted within the outer member. The distal end of the support forms a tip that allows for the passage of fluid there through. The tip is tapered so as to permit safe passage and ease navigation of the elongated section through a lumen or passageway.

The fluid chamber is defined between a first and second seal or valve located within the hollow outer member. The first seal is mounted within the elongated region, proximal to the implant. The second seal is mounted in the truncated section distal to the port. The first and second seals permit fluid flow into the chamber when pressure is applied to the outer member either through the port or the tip depending upon the desired fluid loading method. Once pressure is removed, the seals trap fluid in the chamber forming a fluid column spanning the distance between the shaft and the implant. In one embodiment of the invention the fluid comprises a biocompatible liquid.

The first and second seals permit fluid flow in a single direction during fluid loading. Depending upon whether fluid is loaded from the tip or the port, however, either the first or second seal must also prevent fluid from exiting the chamber when the implant is being deployed. Accordingly, at least one of the seals must toggle between a position where fluid flow is permitted during loading and prevented during deployment of the sheath. A mechanical interface is connected to the relevant seal to toggle between the two flow conditions.

The delivery apparatus is employed to deliver an implant to a desired area within a lumen. As stated above, prior to delivery the apparatus is prepared by loading fluid into the chamber. The apparatus can be prepared in advance of sterilization and packaging. The implant is mounted within the distal end of the elongated section or mounted on the support located within the distal end of the elongated section. Once the implant is mounted, fluid is drawn into the chamber. For example, the tip is placed within a biocompatible liquid and the second seal is toggled to its loading position. Vacuum pressure is applied to the port and liquid is drawn through the tip, past the first seal, into the chamber and exits through the port. Once the chamber is filled, the vacuum is removed and the second valve toggled to its deployment position, trapping fluid in the chamber and forming a column of incompressible fluid.

In an alternate embodiment of the invention, a third seal is mounted within the elongated section, distal to the first seal. The elongated region includes a second port in fluid communication with a section between the first seal and the third seal. The distal end of the elongated region is submersed or placed in fluid communication with a fluid, for example, a biocompatible liquid. Vacuum pressure is applied to the first fluid port, located in the truncated section or region whereby the liquid is drawn through the second port and into the region between the first and second seals. The second seal is toggled between the load and deployment positions during this process permitting and preventing fluid flow accordingly. Alternatively, the port may be submersed in a fluid and vacuum pressure applied to the tip. The second valve would be toggled to accommodate this loading procedure.

In yet another embodiment of the invention, the elongated section includes a guidewire lumen. The guidewire lumen permits a guidewire to pass through the distal end of the elongated region, between the first seal and the tip. The guidewire lumen is in fluid communication with the chamber. The tip is submersed in, or placed in fluid communication with, a liquid. A vacuum is applied to the first port and the liquid is drawn into the chamber through the guidewire lumen. The second seal is toggled to permit and prevent fluid flow during loading and deployment.

Once the implant and fluid column are loaded within the apparatus, the implant is delivered to a desired location within a lumen. The tip is first inserted into the body lumen and advanced, along with the elongated region, such that the implant corresponds to the desired delivery location. The shaft, which is in communication with the fluid column, is held stationary and the outer member, via the handle, is retracted in a proximal direction. As the outer member is retracted, the implant experiences compressive loads that are transmitted distally, along the fluid column. The fluid column stiffens, but due to the incompressible nature of the liquid, resists buckling. The outer member is retracted and the implant is deployed.

BRIEF DESCRIPTION OF THE DRAWINGS

The features and advantages of the invention will be apparent to those of ordinary skill in the art from the following detailed description of which.

DETAILED DESCRIPTION OF THE PREFERRED EMBODIMENTS

Figure 1:
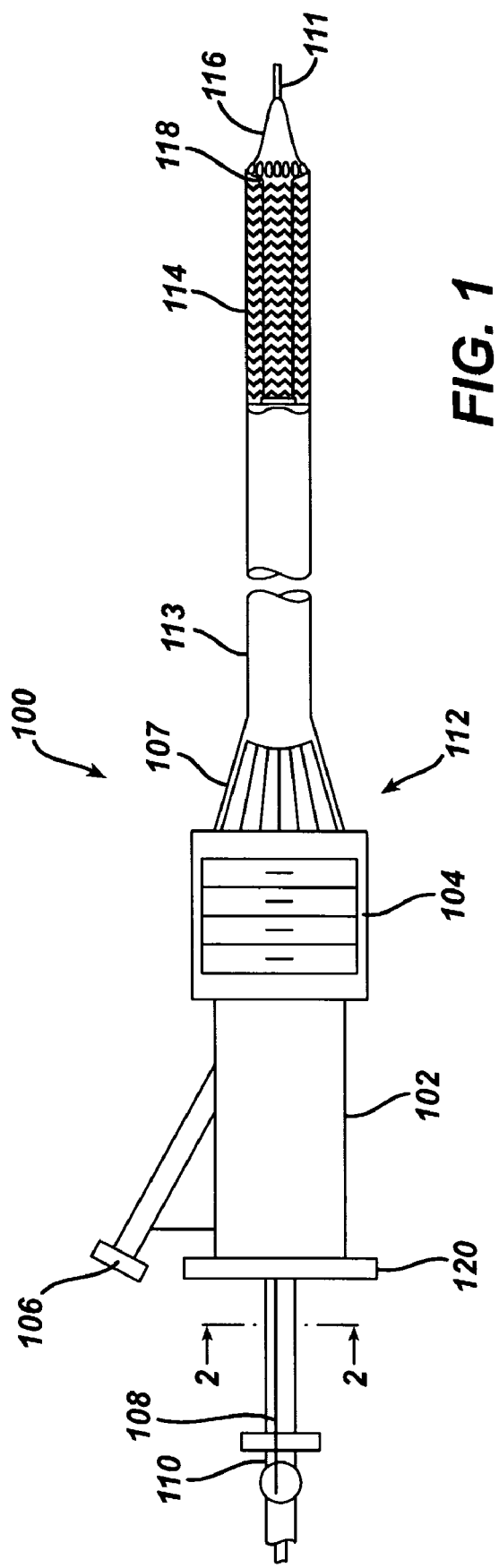
FIG. 1 is a side view of the delivery apparatus of the present invention
Figure 2:
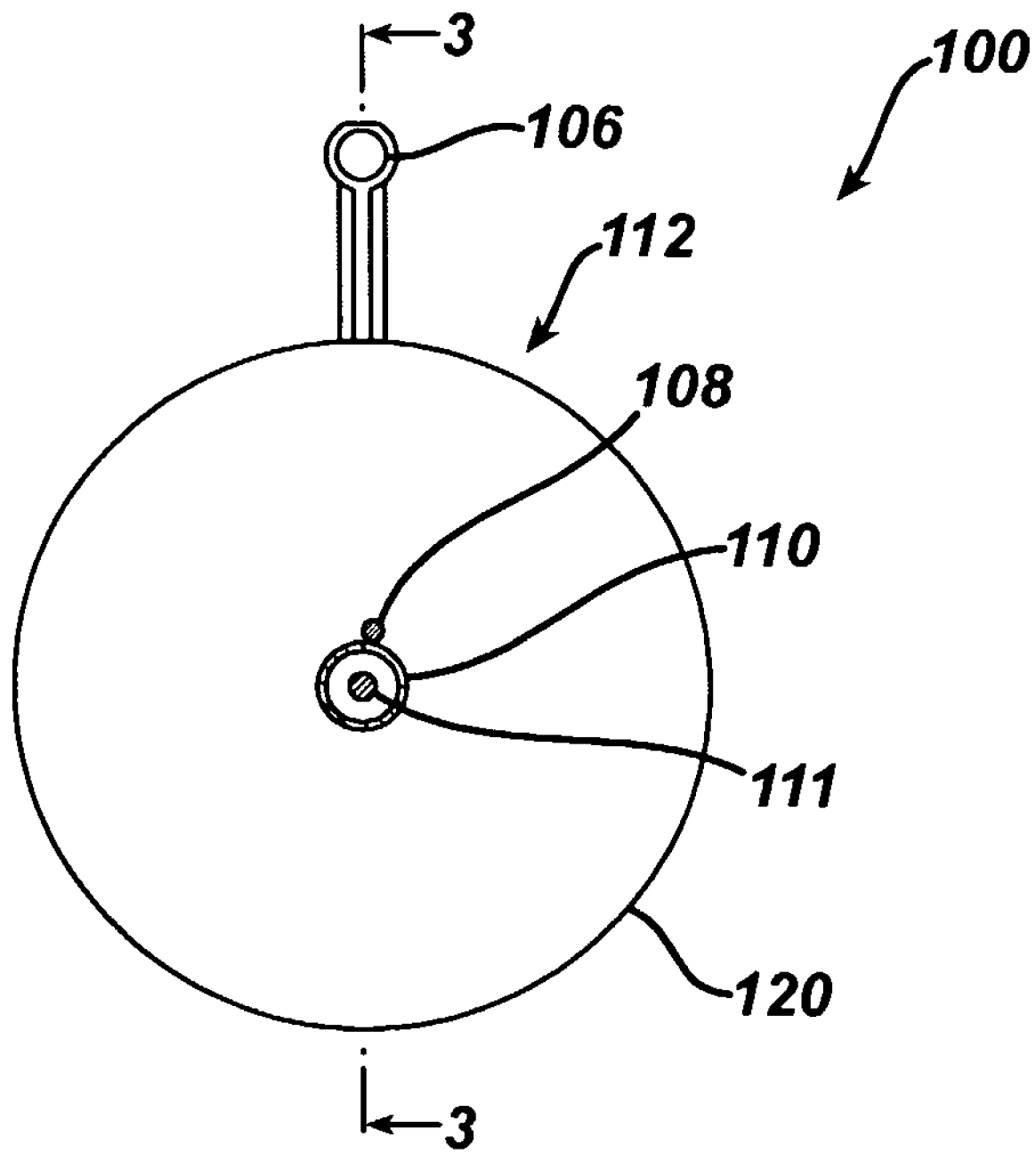
FIG. 2 is a view taken along line 2-2 of FIG. 1 of the delivery apparatus of the present invention.
Figure 3:
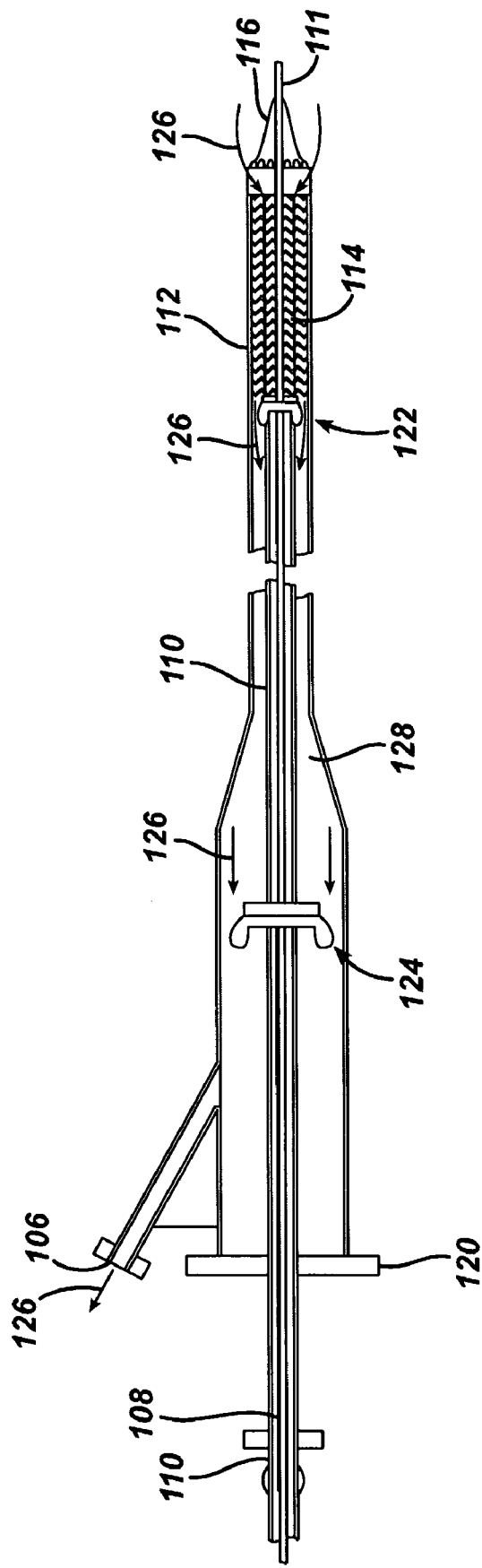
FIG. 3 is a cut away view of the delivery apparatus of the present invention taken along line 3-3 of FIG. 2.
Figure 4:
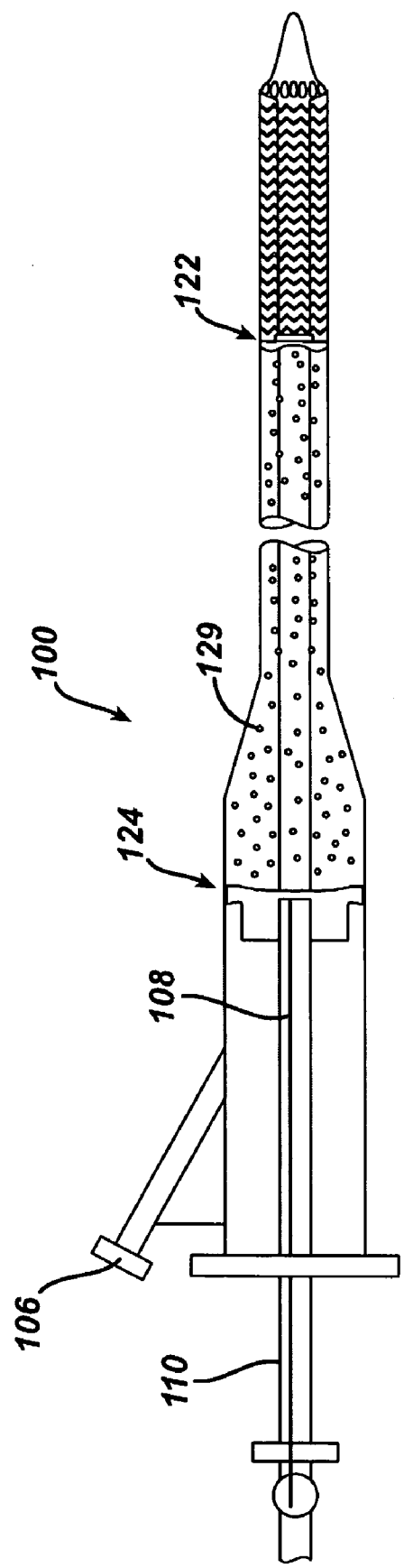
FIG. 4 is a cutaway view of the delivery apparatus of the present invention showing a fluid column.

An apparatus for deploying an implant and methods for preparing and employing the apparatus will be described with reference to FIGS. 1-9. As shown in FIGS. 1-3, the delivery apparatus 100 generally comprises a flexible, hollow outer member 112 that has an elongated section or region 113 that is sufficiently narrow for insertion into, and navigation through, a lumen. An implant 114 is mounted within the distal end of the elongated section 113. Also included within the outer member 112 is a chamber 128 that is located between the implant 114 and a truncated section or region 102 of the outer member 112.

The truncated section has an expanded cross section relative to the elongated section 113 and serves as a handle 102. Handle 102 provides control of the delivery apparatus 100 during insertion and navigation through the lumen and includes a gripping surface 104. Gripping surface 104 can have a tacky surface applied thereto to prevent slippage during navigation and/or deployment of the implant 114. A port 106 is located in the handle 102 and provides fluid communication between the inside and outside of hollow outer member 102. Port 106 is preferably compatible to a syringe or other device that can insert or withdraw fluid from within outer member 102. For example, a Tuohy-Borst valve may be employed.

As shown in FIG. 2, the end 120 of truncated section 102 is closed so as to prevent fluid from escaping from the inside of outer member 112. Openings are provided so that a wire 108 and shaft 110 protrude from the end 120. During loading of the delivery apparatus 100 and deployment of the implant 114, the physician or technician actuates wire 108 and shaft 110, as is described in greater detail below. The delivery apparatus 100 may be steerable or a guide wire 111 may be employed. As shown in FIGS. 1 and 2, apparatus 100 runs over guidewire 111, which protrudes from end 120 and tip 116. Alternatively a rapid exchange system may be employed whereby wire 111 exits proximal to tip 116, not shown in the drawings.

The elongated section or region 113 has the implant 114 mounted at its distal end. Elongated section 113 has a narrow cross section allowing for navigation through small lumens and passages. Elongated section 113 may comprise a substantially cylindrical sheath constructed from a flexible material that is capable of bending during navigation through the lumen or passage, yet can withstand tensile loads exerted by implant 114. For example, a biocompatible polymeric material may be utilized or the elongated section can be constructed from a spun fiber material.

Implant 114 can comprise a wide variety of medical devices and prosthesis designed for insertion into a human body. For example, implant 114 may comprise a self-expanding stent constructed from a superelastic material such as Nitinol (Ni—Ti). Use of superelastic materials allows the stent to be restrained in a deformed condition to facilitate the placement within a lumen. The superelastic characteristics allow the frame to have a first, restricted diameter for mounting within the end of region 113. As the outer member 112 is withdrawn, the stent assumes a second, enlarged diameter.

Figure 7:
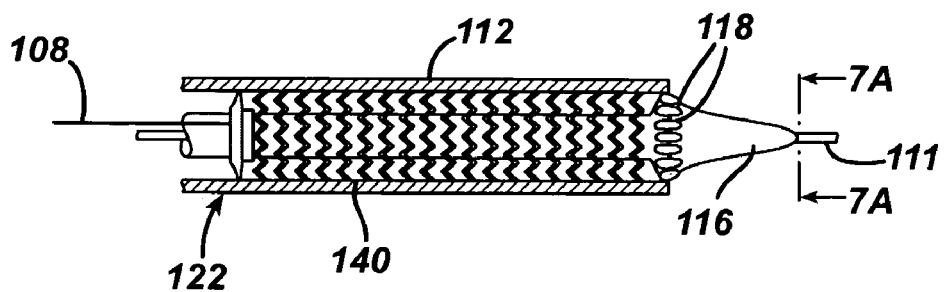
FIG. 7 is a side cutaway view showing an implant mounted on a support of the delivery apparatus of the present invention.
Figure 7A:
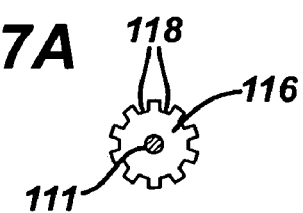
FIG. 7A is a view taken along line 7A-7A showing the tip of the support of FIG. 7.
Figure 8:
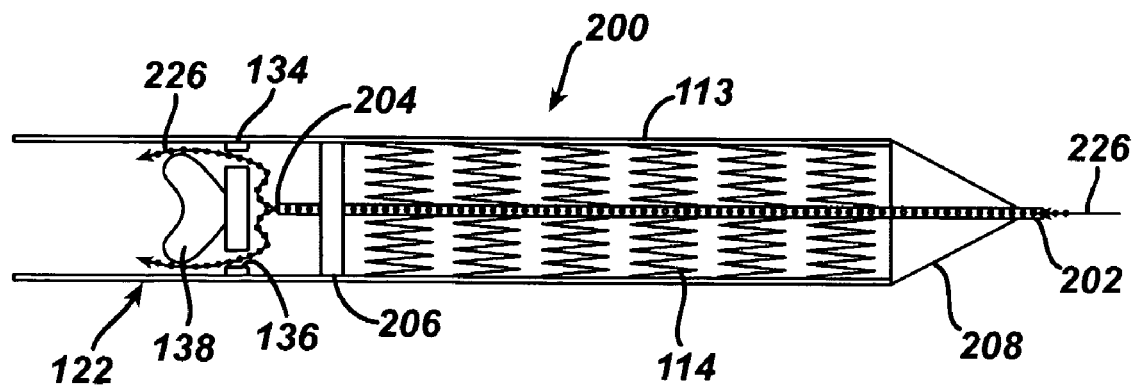
FIG. 8 is a side cutaway view of an alternate embodiment of the delivery apparatus of the present invention.
Figure 9:
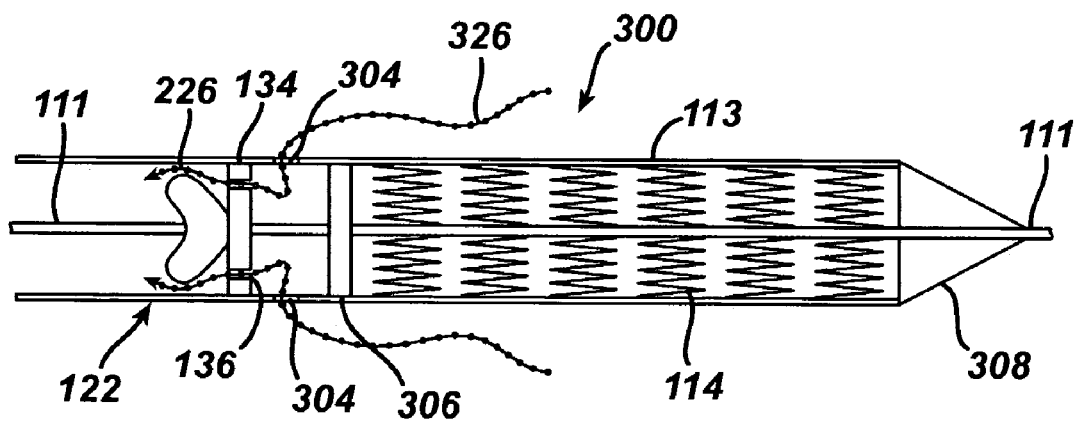
FIG. 9 is a side cutaway view of yet another an alternate embodiment of the delivery apparatus of the present invention.

As shown in FIGS. 1 and 7, implant 114 is mounted on a support 140 located within the distal portion of elongated region 113. The support 140 may comprise a coil or a solid metallic frame. Support 140 carries the compressive load of an implant 114 such as a self-expanding stent when it is contracted within the elongated section 113. The distal end of the support 140 forms a tip 116 that allows for the passage of fluid there through. As shown in FIGS. 7 and 7A, the tip 116 is tapered permitting elongated section 113 to be safely and easily navigated through a lumen. The tip 116 includes at least one notch or flute 118 that allows for fluid to pass through tip 116 into the inside of section 113. In addition, tip 116 includes a port for a guide wire 111. Alternatively, as shown in FIGS. 8 and 9, implant 114 may be mounted within elongated region 113 without the use of support 140. In such an instance, the implant impinges on the walls of the elongated region 113 or is maintained in place between a seal 122, described below, and tip 116.

In most implant delivery devices, it is difficult to optimize the cross section of the device to allow for passage through a lumen and provide sufficient rigidity during deployment. For example, a narrow cross section allows for passage through small lumens. But, during deployment an implant exerts forces that can cause a device with a small cross section to buckle preventing proper deployment of the implant. In the present invention, a fluid column 129 allows for a small cross section while also providing sufficient rigidity during deployment. A fluid chamber 128 is defined between a first or distal seal or valve 122 and a second or proximal seal or valve 124 both located within the hollow outer member 112. The first and second seals 122 and 124 permit fluid flow into the chamber 128 forming a column 129 of incompressible fluid. Fluid may be loaded into the chamber either through the port 106 or the tip 116 depending upon the desired method for placing fluid into the chamber 128. In one embodiment of the invention the fluid placed within chamber 128 is a biocompatible liquid such as saline. The fluid may be loaded into chamber 128 either as a preparatory step by the apparatus user, or alternately, the fluid may be loaded into chamber 128 as part of the pre-sterilization apparatus assembly.

Figure 6:
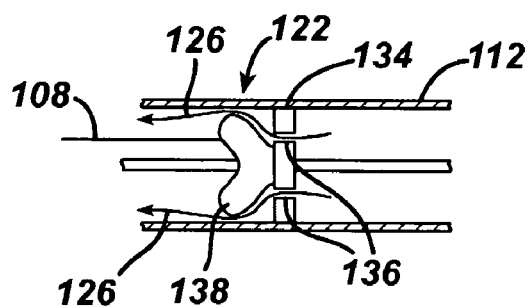
FIG. 6 is a side cutaway view showing another seal or valve of the delivery apparatus of the present invention.

The first seal 122 is mounted within the elongated section 113, proximal to the implant 114. As shown in FIG. 6, the first seal 122 comprises a stop 134 having at least one fluid conduit 136 therein. A flexible member 138 is mounted on the stop 134. Flexible member 138 is biased such that it covers the fluid conduit 136 when pressure is not exerted in a predetermined direction. For example, as shown in FIGS. 3 and 6, when pressure is applied in direction 126, flexible member 138 bends to uncover fluid conduit 136 whereby fluid flow is permitted. Once the pressure is removed, flexible member 138 returns to a position whereby conduit 136 is closed. In one embodiment of the invention, the seal 122 is formed from the proximal end of the support 140.

Figure 5:
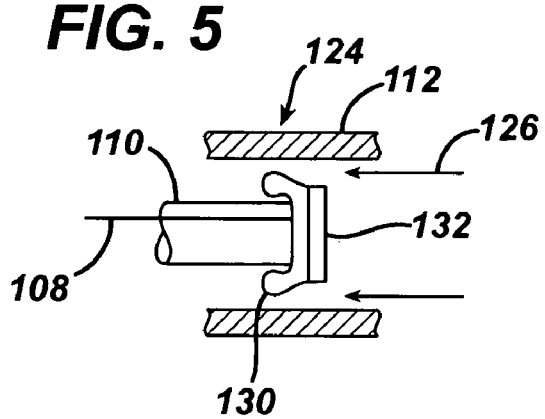
FIG. 5 is a side cutaway view showing a seal or valve of the delivery apparatus of the present invention.

Second seal 124 is mounted within the handle 102, distal to the port 104. As shown in FIG. 5, second seal 124 comprises a fixed member 132 located at the end of shaft 10 having a flexible member 130 attached thereto. Flexible member 130 is biased opposite direction 126. During deployment of the implant 114, the second seal 124 must also prevent fluid from exiting the chamber 138. The second seal 124 toggles between a position where fluid flow is permitted during loading and prevented during deployment of the sheath. A mechanical interface is connected to the relevant seal to toggle between the two flow conditions. The interface is accessible from outside of the outer member 112. In one embodiment of the invention, the interface comprises a tether wire 108, which is attached to the flexible member 130. As described above, the tether wire 108 extends outside of handle 102. Pulling on the wire 108 pulls the flexible member 130 in direction 126 allowing for fluid flow through valve or seal 124. Releasing the tether wire 108 returns the flexible member to a closed position for the deployment of implant 114.

Prior to delivery of implant 114, apparatus 100 must be prepared by loading fluid into the chamber 128. The implant 114 is first mounted within the distal end of section 113 or mounted on the support 140 located within the distal end of the elongated section 113. As shown in FIG. 3, fluid is drawn into the chamber 128 through tip 116. In order to accomplish this, tip 116 is placed within a biocompatible liquid and second seal 124 toggled to its loading position by pulling wire 108 proximally. Vacuum pressure is applied to the port 106 by a syringe or other source of pressure and the flexible member 138 of first seal open conduits 136. Liquid is drawn through the tip 116, past the first seal 122, into the chamber 128 and then exits through the port 106 in direction 126. Once the chamber 128 is filled, the vacuum is removed and the second valve 124 toggled to its deployment position, trapping fluid in the chamber 128 and forming a column 129 of incompressible fluid.

Alternatively, second seal 124 may be toggled to its loading position and fluid injected into the chamber through port 106, opposite direction 126. Upon filling the chamber 128, the second seal 124 is toggled to its deployment position, trapping fluid inside the chamber 128 and forming column 129. Yet another alternative is to inject fluid into tip 116, leaving second seal 124 in its deployment position trapping fluid in chamber 128.

An alternate embodiment of the invention is shown in FIG. 8. Delivery apparatus 200 is substantially as described above, but apparatus 200 includes a seal or stop 206 mounted within the elongated section 113, distal to the first seal or valve 122. In addition, elongated section 113 includes a guidewire passageway 202. The guidewire passageway 202 permits a guidewire 111 to pass through the distal end of the elongated section 113, between the first seal or valve 122, the stop 206 and the tip 208. Alternatively, the apparatus 100 or 200 may be configured for a rapid exchange system. Passageway 202 is in fluid communication with chamber 128. For example, passageway 202 includes outlet 204 that permits fluid to flow in the area between first valve 122 and seal or stop 206. Fluid loading of apparatus 200 may be accomplished through the methods described above.

Yet another embodiment of the delivery apparatus 300 is shown in FIG. 9. A seal or stop 306 is mounted within the distal end of the elongated section 113, distal to the first seal or valve 122. The elongated section 113 includes a port 304 in fluid communication with a region between the first seal or valve 112 and the stop or seal 306. The distal end of the elongated section 113 is submersed or placed in fluid communication with a biocompatible liquid. Second seal 124 is toggled to a load position and vacuum pressure is applied to the fluid port 106, located in the truncated section or handle 102 whereby the liquid is drawn through the port 304 past the seals 122 and 124 and into the chamber 128. The second seal 124 is toggled to its implant 114 deployment position and fluid column 129 is formed.

Once fluid column 129 is formed and implant 114 mounted within the distal end of elongated section 113 the apparatus is prepared to deliver the implant 114. Where the lumen or passageway is a human blood vessel, the tip 116 is first inserted into the lumen of the vessel by any of a variety of methods known to those of skill in the art. The tip 116 and elongated section 113 are advanced within the lumen of the vessel until the implant is positioned at the desired location. The shaft 110, which is in contact with fluid column 129, is held in a stationary position. The handle 102 is gripped and pulled in a proximal direction, correspondingly moving elongated section 113 proximal to the implant 114. As the elongated section 112 is retracted, the implant 114 experiences compressive loads that are transmitted proximally along the fluid column 129. Where the implant 114 comprises a self-expanding stent, withdrawing the elongated section 113 allows the stent to expand and deploy within the lumen. Once deployment is complete, the shaft 110 is released and the handle 102 pulled distally withdrawing the elongated section 113 from the lumen of the vessel.

Although the present invention has been described above with respect to particular preferred embodiments, it will be apparent to those skilled in the art that numerous modifications and variations can be made to these designs without departing from the spirit or essential attributes of the present invention. Accordingly, reference should be made to the appended claims, rather than to the foregoing specification, as indicating the scope of the invention. The descriptions provided are for illustrative purposes and are not intended to limit the invention nor are they intended in any way to restrict the scope, field of use or constitute any manifest words of exclusion.

What is claimed is:

1. An apparatus for delivering an implant within a lumen comprising:
   a hollow outer member having an elongated first region and a second region located proximal to the elongated first region, the first region having an implant region at the distal end thereof, the implant region being configured to accept the implant;
   a first seal located within the first region proximal to the implant region, wherein the first seal comprises a stop having at least one fluid conduit therein and a first flexible member mounted on the stop covering the at least one fluid conduit, whereby when said first flexible member is actuated in a first direction fluid flow is permitted through the at least one fluid conduit;
   a second seal located within the second region, the second seal comprising a fixed member having a second flexible member attached thereto, wherein actuating said second flexible member in a first direction allows fluid to pass between the second flexible member and an inner wall of the outer member, the first seal and the second seal forming a chamber there between, wherein the first and second seals permit fluid flow in a single direction forming a liquid column within the chamber, the liquid column being adapted to receive compressive loads that are transmitted proximally along the fluid column;
   a tether wire attached to the second flexible member and extending outside the outer member whereby pulling the wire in a proximal direction actuates the second flexible member allowing fluid flow past the second flexible member, and releasing the tether wire closes the second flexible member preventing fluid flow there through; and
   a shaft mounted within the outer member and extending from at least a proximal end of the second region to the second seal.

2. The apparatus of claim 1 wherein the first region of the outer member has a cross section that allows passage within the lumen of a body vessel.

3. The apparatus of claim 2 wherein the second region of the outer member has an expanded cross section so as to form a handle, the first region being connected to the second region by a tapered section.

4. The apparatus of claim 3 wherein the handle includes a port in fluid communication with the inside of said second region.

5. The apparatus of claim 3 wherein the handle includes a gripping surface.

6. The apparatus of claim 1 wherein said implant comprises a self-expanding stent.

7. The apparatus of claim 6 wherein the outer member comprises a sheath constructed from a flexible material capable of maintaining the self-expanding stent in a constrained position.

8. The apparatus of claim 7 wherein a biocompatible, incompressible fluid is present between the first and second seals prior to the sterilization of the apparatus.

9. The apparatus of claim 1 further comprising a support located within the distal end of the first region, the support having a tip with at least one flute located thereon wherein the implant is mounted on the support between the tip and the first seal.

10. The apparatus of claim 1 wherein the stop is formed from a proximal end of a support, the support extending along the distal end of the first region and having the implant mounted thereon.

11. The apparatus of claim 1 wherein a fluid port is located on the second region and is in fluid communication with the inside of outer member such that when negative pressure is applied to the fluid port the first and second seals are actuated to permit fluid flow into the chamber.

12. The apparatus of claim 11 wherein when the chamber is filled with fluid, the seals are actuated to prevent fluid from flowing out of the chamber creating an incompressible fluid column.

13. The apparatus of claim 12 wherein the fluid comprises a biocompatible fluid.

* * * * *